(12) United States Patent
Carr et al.

(10) Patent No.: US 6,274,542 B1
(45) Date of Patent: Aug. 14, 2001

(54) PERCARBOXYLIC ACID SOLUTIONS

(75) Inventors: Graham Carr; Alun P. James, both of Liverpool; Kelly J. Morton, Widnes; John P. Sankey; Valerie Lawton, both of Warrington, all of (GB)

(73) Assignee: Solvay Interox Limited (GB)

( * ) Notice: Subject to any disclaimer, the term of this patent is extended or adjusted under 35 U.S.C. 154(b) by 0 days.

(21) Appl. No.: 09/331,395

(22) PCT Filed: Dec. 16, 1997

(86) PCT No.: PCT/GB97/03461

§ 371 Date: Nov. 2, 1999

§ 102(e) Date: Nov. 2, 1999

(87) PCT Pub. No.: WO98/28267

PCT Pub. Date: Jul. 2, 1998

(30) Foreign Application Priority Data

Dec. 21, 1996 (GB) .................................................. 9626637

(51) Int. Cl.[7] .............................. C11D 3/00; C11D 3/395; C11D 7/18; C11D 7/54
(52) U.S. Cl. ......................... 510/376; 510/372; 510/375
(58) Field of Search .................................... 510/376, 375, 510/372

(56) References Cited

FOREIGN PATENT DOCUMENTS

| 0 166 571 | 1/1986 | (EP) . |
|---|---|---|
| 0 426 217 | 5/1991 | (EP) . |
| 2 324 626 | 4/1977 | (FR) . |
| 95/34537 | 12/1995 | (WO) . |

OTHER PUBLICATIONS

Nedelec, et al.; "Preparation of Peroxycarboxylic Acids", Centre Nat'l de la Recherche Scienftifiques, Dec. 1976.

Hedayatullan et al.; "Nouveaux Decontaminants Action . . . ", Bull. Soc Chm. Beig. vol. 100 No. 7, 1991 (European Section).

*Primary Examiner*—Necholus Ogden
*Assistant Examiner*—John M Petruncio
(74) *Attorney, Agent, or Firm*—Larso & Taylor, PLC

(57) ABSTRACT

Storage stable aqueous acidic solutions, often having a pH of up to 1 containing an ester peracid and/or an acid peracid can be obtained by reacting a diester satisfying the general formula $R^1$—O—CO—$R^2$—CO—O—$R^3$ in which $R^1$ and $R^3$ each represents a alkyl group containing from 1 to 4 carbon atoms which may the same of different and $R^2$ represents an aliphatic alkylene group optionally unsaturated which may be linear or branched containing from 2 to 6 carbon atoms with aqueous hydrogen peroxide in the presence of an acid, such as sulphuric acid and permitting the compositions to progress towards equilibrium concentrations. By starting with a diester, perhydrolysis generates an ester peracid which is a particularly effective peracid. The process can be controlled to produce solutions containing a high peracid content and within a wide range of ratios of ester peracid to acid peracid.

52 Claims, No Drawings

PERCARBOXYLIC ACID SOLUTIONS

This invention relates to percarboxylic acid solutions and more particularly to their production from precursors comprising carboxylic acid esters.

Percarboxylic acids, by virtue of their properties, are contemplated for application in a wide range of uses, for example as oxidants, as stain removers and as microbicides, amongst others. Many factors are taken into account in selecting which percarboxylic acid is employed for a particular application, including its effectiveness for the purpose, its ease of preparation, its stability, and its acceptability to the user. For example, a low molecular weight aliphatic monoperoxyacid such as peracetic acid has been the peracid of choice on a number of occasions, because it can be produced readily, is acknowledged to be effective and capable of being produced in stable solutions, and is acceptable to many users, but some producers of microbicidal compositions would prefer to employ a compound with less odour, in order to avoid possible offence or irritation to the final users of those compositions.

A number of alternative percarboxylic acids have been disclosed hitherto in the literature that are derivable from dicarboxylic acids and derivatives thereof, including diperoxycarboxylic acids, their corresponding monoperoxy acids, and ester monoperoxycarboxylic acids.

For example, European Patent application No. EP-A-0 166 571 to Unilever teaches the use of ester peracids of the general formula $[RX]_m AOOH$, where R is hydrocarbyl or alkoxylated hydrocarbyl, X is a heteroatom moiety, preferably oxygen, A is a wide range of organic moieties containing one or two carbonyl groups and m is one or two, for use in bleaching and laundry applications.

European Patent Application No. EP-A-0 426 217 to Unilever teaches the use of ester peracids of the general formula $X—O_2C—A—CO_3H$ where A is a C1 to C12 alkyl aryl or alkaryl radical and X is a C1 to C20 alkyl, aryl, alkyl aryl radical optionally including a heteroatom for use in bleaching and cleaning systems.

Both French Patent Application no. 2324626 and a paper by Nedelec et al, Synthesis, 1976, pp 821–3 teach a method for the preparation and isolation of ester peracids from the reaction between acid chlorides and hydrogen peroxide in organic solvents.

A paper by C. Lion et al. Bull. Soc. Chim. Belg. 1991, 100, pp.-559 discloses the preparation and isolation of ester peracids by the reaction between ester acid and hydrogen peroxide in the presence of high concentrations of sulphuric acid and quenching into ice. The ester peracids so produced are employed in the destruction of toxic organophosphorus compounds in aqueous alkaline solution.

Compositions containing ester percarboxylic acids and their preparation by reaction between a monoester of an aliphatic dicarboxylic acid and hydrogen peroxide have been described in a PCT Application, International Publication WO 95/34537 to Solvay Interox Limited. Such compositions were shown to have no discernible odour and to be effective as a microbicide. Although the compositions exhibited a level of available oxygen (avox) stability that would enable to them to remain effective during several weeks storage, there is a continuing need to find ways of improving their storage capability, for example based on the total peracid content or total peroxygen content of the composition and/or extending the range of reagents from which they or related compositions can be produced.

It is an object of at least certain aspects of the present invention to provide a new or alternative process for the production of peracids of aliphatic dicarboxylic acids and their esters.

According to the present invention, there is provided a process for the production of aqueous percarboxylic acid solutions by reaction between a peroxygen compound and a precursor of the percarboxylic acid in the presence of an acid catalyst characterised in that the peroxygen compound is hydrogen peroxide and the precursor is an aliphatic diester satisfying the general formula $R^1—O—CO—R^2—CO—O—R^3$ in which $R^1$ and $R^3$ each represents an alkyl group containing from 1 to 4 carbon atoms which may the same or different and $R^2$ represents an aliphatic alkylene group which may be linear or branched containing from 2 to 6 carbon atoms and optionally unsaturated.

The selection of hydrogen peroxide to effect the peroxidation avoids the neutralisation or partial neutralisation that would arise if an alternative inorganic peroxygen compound like sodium percarbonate or sodium perborate were employed.

In a further aspect there is provided a composition comprising an ester, a peracid derivative of thereof, hydrogen peroxide and water characterised in that it comprises from 2 to 30% w/w hydrogen peroxide, 5 to 90% w/w water and 3 to 90% w/w of an aliphatic diester satisfying the general formula $R^1—O—CO—R^2—O—R^3$ in which $R^1$ and $R^3$ each represents an alkyl group containing from 1 to 4 carbon atoms which may the same or different and $R^2$ represents an alkylene group which may be linear or branched containing from 2 to 6 carbon atoms and optionally unsaturated, the % for the diester including the peracidic derivative thereof and any acidic derivative of the ester generated in situ.

Herein the compositions are often expressed in terms of the reactants that are introduced into the reaction mixture, namely the diester and hydrogen peroxide. It will be recognised that in the reaction mixture, a number of acid catalysed hydrolysis and perhydrolysis reactions take place, resulting in a complex mixture containing a residual concentration of the reactant diester, the corresponding monoester peroxycarboxylic acid in which one or other of $R^1$ and $R^3$ groups have been substituted to convert the ester to a peroxyacid group and likewise the corresponding monoester carboxylic acid, and the corresponding diperoxycarboxylic acid in which both $R^1$ and $R^3$ groups have been substituted to convert the ester to a peroxyacid group and likewise the corresponding dicarboxylic acid. As the reactions proceed, the mixture moves towards an equilibrium at which point the relative proportions of each constituent of the mixture depend on the relative proportions and concentrations of the diester and the hydrogen peroxide employed in the mixture before equilibration commences and the extent of decomposition of the peroxygen compounds subsequently. The rate at which the composition moves towards equilibrium depends on the prevailing temperature, the concentrations of the reactants and the concentration of the catalyst.

By controlling the composition of the reaction mixture expressed in terms of its reagents, and specifically by the choice of molar ratio of the diester to hydrogen peroxide and the extent of dilution of the mixture with water, it is possible to control the ratio of monoester monopercarboxylic acid to other monopercarboxylic acid/dipercarboxylic acid constituents at equilibrium and during the move towards equilibrium. In particular the peroxygen species can be directed towards the acid/monoperacid as the main or predominant peroxyacid species by diluting the mixture with at least a significant or preferably with a major fraction of water. The peroxyacid species can be directed towards the ester monoperacid species by employing high concentrations of the diester and hydrogen peroxide, preferably at or near an equimolar ratio and comparatively low concentration of water. During the period in which the mixture is approaching equilibrium, the proportion of peroxygen species, as measured by the proportion of available oxygen (Avox), present as peroxyacid species increases. Since, for many purposes, peroxyacid species are more effective as eg a biocide or oxidant, it is desirable to store the mixture until a significant fraction of the developable peroxyacid species have been produced, such as at least 90% before use.

It will be recognised that there is a particular benefit in employing diester derivatives of dicarboxylic acids as substrate for the formation of peracid derivatives, namely that first perhydrolysis de-esterification reaction of such a substrate generates an ester peracid (a percompound containing an ester group and a peracid group) which has been found to be a particularly effective disinfectant compared for example with the corresponding acid peracid (a percompound containing a carboxylic acid group and a peracid group). Accordingly there is an immediate generation of the more effective peracid species from the diesters. By contrast, if a monoester derivative of a dicarboxylic acid is employed as substrate, the first perhydrolysis de-esterification reaction generates the acid peracid. It is highly desirable to produce compositions from diester substrates containing at least 0.1% and preferably at least 0.2% ester peracid. In a number of compositions according to the present invention, the ester peracid content is in the region of 0.3 to 3% w/w, and particularly in the region of 0.6 to 1.5% w/w, even after storage for several weeks such as 3 to 6. It is beneficial to select compositions containing at least 0.1% or preferably a higher concentration of ester peracid.

In a yet further aspect of the invention, there are provided compositions containing hydrogen peroxide, a peracid and an ester and hydrolysis and/or perhydrolysis derivatives thereof characterised in that they comprise at least 2% w/w hydrogen peroxide, preferably 2 to 30% w/w, at least 3% w/w diester including hydrolysis and perhydrolysis derivatives thereof, preferably 3 to 90% w/w, of which at least 0.1 and preferably at least 0.2% w/w is an ester peracid.

The compositions produced from a diester and hydrogen peroxide will contain a residual concentration of hydrogen peroxide which will approach an equilibrium. Since hydrogen peroxide itself also enjoys bleach, oxidation and disinfectant properties, though often inferior to generated peroxyacid species, it is desirable to preserve the hydrogen peroxide content of the composition as well as encourage formation of peracids. The ability of the composition to preserve the content of the peroxygen species during preparation and storage of the compositions can be observed by measuring the total available oxygen (avox) retained in the composition and comparing it with the amount introduced in the hydrogen peroxide Advantageously, it has been found that the invention process employing a diester peracid generator is a particularly effective means of preserving the avox of the resultant compositions.

The invention often employs fully saturated diesters, though it can employ unsaturated starting materials, such as the diesters of fumaric or maleic acid.

The present invention is particularly applicable to the production of peroxyacid-containing mixtures from diesters of linear dicarboxylic acids and especially to those in which $R^2$ in the above-mentioned formula contains from 2 to 4 carbon atoms and to mixtures of any two or all three of them. An especially convenient diester starting material contains a mixture of diesters of succinic acid (10 to 20% w/w), glutaric acid (45 to 75% w/w) and adipic acid (20 to 33% w/w). The alkyl groups $R^1$ and $R^3$ are often either methyl or ethyl. It is often convenient for them to be the same, both within the same molecule and also in mixtures of dicarboxylic acids esters, but they can be different if desired and mixtures of different alkyl groups for $R^1$ and $R^3$ can be employed. It is particularly desirable to employ dimethyl esters. A particularly convenient starting material comprises a mixture of the dimethyl diesters of succinic, glutaric and adipic acids. Other convenient starting materials comprise, for example, the dimethyl esters of the individual components of that mixture, such as dimethylsuccinate.

The invention process can be carried out at ambient temperature or at an elevated temperature, which in practice often means employment of a temperature selected within the range of from 10 to 50° C. Use of a yet higher temperature tends to accelerate noticeably loss of available oxygen from the compositions. In many instances, either the entire production and storage equilibration period or the storage equilibration period alone is conducted at a temperature of between 15 and 30° C. Depending on the reagent and catalyst concentrations, as well as employing an elevated temperature, equilibration can achieved at its shortest within a few hours and under less favourable conditions, equilibration can take several weeks. It is at the discretion of the producer as to the extent to which he adjusts the conditions to accelerate progress towards equilibration compared with progress at ambient. He may, in one variation, employ an elevated temperature such as from 30 to 50° C. for a short period of for example 1 to 10 hours and for the remainder employ the natural ambient temperature of the mixture.

The acid catalyst is an inorganic or organic acid having a $pK_a$ of about 3 or lower, and preferably having a $pK_a$ of below 1. It is particularly desirable to employ a non-halide mineral acid such as sulphuric or phosphoric or sulphamic acid or an organic sulphonic acid such as methyl or toluene sulphonic acid or a cation exchange resin doped with acid (eg a resin available under the Trade Mark AMBERLITE IRA-93), The catalyst is desirably present at a concentration of from 0.05 to 10% w/w in the composition and in many instances from 0.1 to 2.5% w/w When it is desired to produce solutions containing a relatively high concentration of peracid species, thereby employing reaction mixtures containing a major weight proportion of diester, it can be prudent to select the concentration of strong acid in inverse relationship to the concentration of hydrogen peroxide employed. This relationship can be described by the formula H×C=60 to 150 and preferably 80 to 120, in which H is the weight concentration of hydrogen peroxide solution introduced, usually selected in the range of 50 to 85%, and C is the weight concentration of catalyst in the composition, usually selected in the range of from 0.75% to 2.25%. It will also be recognised that the strong acid can perform additional functions, depending on its concentration, such as improved lime-scale removal when present at a relatively high concentration, such as from 5 to 100% w/w of the composition.

The absolute amounts of diester and hydrogen peroxide and their ratio to each other in the reaction mixture can be varied within a wide range. It is strongly recommended that in addition to any other criteria mentioned herein, the absolute concentrations of the organic and hydrogen peroxide constituents within the mixtures are preferably selected so to avoid potentially hazardous combinations by adoption existing guidelines for organics/peroxide/water compositions. As a general guide, it is highly preferable not to exceed at any time a hydrogen peroxide concentration of 30% w/w and preferable not to exceed 20% w/w. It is often desirable to employ at least 1 mole of hydrogen peroxide per mole of diester. In many instances, the hydrogen peroxide concentration in the mixture is selected in the range of from at least 2%, w/w, often at least 4%, w/w and, particularly, up to 16% w/w. It can be introduced into the composition at either a concentration calculated to achieve the desired concentration after mixture with remaining constituents or at a higher concentration to enable the balance of water to be added to achieve the desired concentration. In general, the proportion of diester in the reaction mixture is selected within the range of from about 3% w/w and often at least 5% w/w to 90% w/w In a number of embodiments, the proportion of diester in the mixture is selected in the range of at least 50%, particularly from about 70 to 85% by weight and especially from about 75 to 85% by weight, together with aqueous hydrogen peroxide providing up to 20% w/w $H_2O_2$ Preferably the amount of hydrogen peroxide is at least equimolar to the diester. By the choice of at least 70% of diester in the initial composition, it is usually possible to retain throughout the reaction the mixture as a one-phase system. It is particularly desirable to select in combination from around 75 to 85% diester and from 1 to 1.25 moles of hydrogen peroxide per mole of diester. In such embodiments, the mixture can generate, at equilibrium, desirably high concentrations of peracids and such conditions favour the generation preferentially of monoester peracids. Such peracids have been found to be particularly acceptable for employment in cleanser/disinfectant compositions in view of their capability to act as bleach oxidant for stains, their microbicidal properties and the absence of off-putting odours. In a number of these embodiments, the peracid concentration is high enough to provide a peracid avox in solution at equilibrium of between 1.5 and 3.5% by weight, which corresponds to a peracid concentration of between about 15 and 35% depending on the peracid avox itself and the peracid species present. It will be recognised that the concentrated compositions can be diluted by the presence of a minor amount of additional components to assist in wetting or cleansing of surfaces or articles or liquids, such as up to about 20% by weight of surfactants.

In other embodiments of the present invention, the compositions are relatively dilute, often containing from 50 to 90% water, in a number of instances at least 60% by weight of water, and in many instances at least 70% by weight of water, such as from 70 to 85% by weight of water. In such dilute embodiments, the compositions, initially, that is to say before equilibration commences, often contain hydrogen peroxide selected in the range of form at least 2% w/w and particularly 4 to 25% by weight and diester selected in the range of from at least 3% w/w and particularly 5 to 45% by weight. The weight ratio of diester to hydrogen peroxide initially in such dilute embodiments is often chosen in the range of from 4:1 to 2:3. Accordingly, in a number of selected embodiments, the proportion of water initially is from 75 to 85%, and the proportion of hydrogen peroxide is initially from 4 to 12% and the proportion of diester initially from 5 to 15%. In such compositions there is a greater propensity for the peracid species generated to comprise a significant fraction of acid peracid species in addition to monoester peracid species. As with the more concentrated embodiments, one or more surfactants can be incorporated, such as in amount of up to 20% often up to 10% by weight of the composition.

In yet further embodiments of the present invention, the producer can produce compositions which, if permitted to attain equilibrium, would have an intermediate water content, such as between 20 and 50%, an intermediate peracid avox concentration in the region of between about 0.5 to 1.2%. In such compositions the initial weight proportion of diester is often from 10 to 60% and the weight proportion of hydrogen peroxide is often from 10 to 30%.

In a further variation carried out in a plurality of stages, more concentrated reagents are employed in a first stage, and when the composition peracid content has progressed to a chosen intermediate fraction of that attainable at equilibration, in a second stage, the composition is diluted by introduction of sufficient water, and optionally hydrogen peroxide and/or diester and and/or preformed esteracid to prepare a more dilute composition, such as those described previously herein which desirably contain at least 50% water and of which many contain at least 75% water. Examples of such dilute compositions which can be prepared by the two stage route contain the concentrations and ratios of peracids, residual ester and hydrogen peroxide that are obtainable using the preferred dilute concentrations of hydrogen peroxide and diester before equilibration described hereinbefore. In the first stage, the reaction mixture expressed in terms of its reactants desirably comprises at least 50% w/w diester and at least 1 mole of hydrogen peroxide per mole of diester, preferably at least an equimolar amount. The mixture is preferably stored until at least 75 molar % and more preferably at least 90 molar % of the equilibrium proportion of peracid species is attained. Preferably in the second stage, the amounts of diluent water, added reagents and optionally selected reaction products are so chosen as to produce a composition that is substantially at equilibrium or contains esteracid at above its equilibrium amount if produced in a single stage.

Amongst the variations in methods for producing the aqueous percarboxylic acid solutions of the present invention, and especially for producing compositions which contain a substantial fraction of water, such as those containing at least 50% by weight water, one variation which offers processing advantages comprises a two stage method, in the first stage of which aqueous hydrogen peroxide and the diester are agitated together to form a single phase, normally containing any stabilisers and optional surfactant, and in the second stage, the phase is diluted with water and optional constituents such as lime-scale remover and once again agitated until a single phase is obtained. It is especially desirable to conduct this process variation at above ambient temperature, such as from about 30 to 45° C. In this process variation, it is particularly beneficial to employ aqueous hydrogen peroxide which has a concentration selected in the range of from about 27% to 55% by weight $H_2O_2$ and especially 33 to 40% by weight $H_2O_2$. It is of benefit to introduce the aqueous hydrogen peroxide gradually into the ester, and especially at a rate controlled such that the composition remains as a single phase. Likewise, when the aqueous hydrogen peroxide has been introduced, the water can be introduced at a rate similarly controlled to maintain a single phase. It will be recognised that the water introduction can commence before the hydrogen peroxide introduction has terminated, but that in such circumstances, it is preferable to control the rates of introduction of both constituents together to maintain a single phase.

It is an observed feature of the present invention that ester peracid generation from glutaric acid esters is favoured in comparison with its generation corresponding succinic or adipic acid esters, particularly when the diester constitutes the major weight fraction of the reaction mixture.

It is preferable to choose surfactants for incorporation into peracid compositions according to the present invention, whether they be concentrated or dilute, which are compatible with peracid compositions, such as those described in WO 96/19558 to Solvay Interox Limited. Herein the surfactants can be incorporated into preformed peracid solutions or present during the formation of the peracid solutions from the reagents. Advantageously, if suitably chosen amounts and combinations of such surfactants as described therein are employed, they can perform additional functions such as thickening and can aid disinfection. Suitable classes of surfactants as described therein include non-ionic surfactants and particularly alcohol ethoxylates, anionic surfactants such as alkylsulphates and alkyl-benzene sulphonates, amine oxides and quaternary ammonium surfactants.

Although the compositions produced by the invention process demonstrate a stability worthy of mention, for example by comparison with previously described methods for their preparation from other peracid precursors, including expressly the preparation of peracid compositions from monoesteracid compounds, their stability can be enhanced by the incorporation of a number of classes of compound identified below. These classes include hydroxy substituted aromatic carboxylic acids and ester derivatives thereof, particularly phenol carboxylic acids such as p-hydroxybenzoic acid and ester derivatives such as methyl or ethyl esters. They also include organic polyphosphonic acid sequestrants such as ethylidene diphosphonic acid, and aminopolymethylenephosphonic acids, and mixtures thereof. Such compounds are often incorporated in an amount selected in the range of from 0.025 to 1%, and in many instances from 0.075 to 0.3% by weight of the composition.

The surfactants which can be employed herein can be nonionic, anionic, cationic, or amphoteric. Generally, the surfactants contain at least one hydrophobic group, e.g. an aliphatic hydrocarbon group containing at least 8 carbon atoms, and often from 10 to 26 carbon atoms the aliphatic group often being acyclic, but sometimes containing an alicyciic group, or the hydrophobic group can be an alkaryl group containing at least 6 and preferably up to 18 aliphatic carbon atoms. The surfactant contains in addition at least one water-solubilising group for example a sulphonate, sulphate, or carboxylic group which is linked either directly or indirectly to the hydrophobic group. Linking members can include residues of polyhydric alcohols containing etheric or esteric linkages, for example derived from ethylene glycol, propylene glycol, glycerine or polyether residues. The surfactants can be soap or be synthetic, for example as described in chapter 2 of synthetic Detergents by A. Davidsohn and B. M. Milwidsky, 6th Edition published in 1978 by George Godwin Limited, and methods of making them are described in chapter 5 of the same book. Amongst anionic surfactants described on pages 11–23 of the aforementioned book, sulphonates and sulphates are of special practical importance. The sulphonates include, for example, alkaryl sulphonates, and particularly alkyl benzene sulphonates, the alkyl group preferably being a straight chain containing 9 to 15 carbon atoms, of which one of the most commonly employed surfactants is linear dodecyl benzene sulphonate. Other anionic sulphonates which are useful in solutions herein include olefin sulphonates, obtained, for example, by sulphonating primary or secondary aliphatic mono-olefins, alkane sulphonates, especially linear alkane sulphonates, and hydroxy alkane sulphonates and disulphonates, especially 3-, 4-, and 5-hydroxy-n-alkyl sulphonates in which the alkyl group contains any even number from 10 to 24 carbon atoms. Other desirable anionic surfactants include alcohol sulphates, preferably linear, having a chain length of at least 10 carbon atoms and sulphated fatty acid alkanolamides. Other sulphates comprise sulphated nonionic surfactants as for example alkylphenoxyethylene oxide ether sulphate in which the alkyl groups contain from about 8 to 12 carbon atoms and there are 1 to 10 units of ethylene oxide in each molecule. Yet other sulphate surfactants comprise alkyl ether sulphates where the alkyl group contains from 10 to 20 carbon atoms, preferably linearly and each molecule contains from 1 to 10 preferably from 1 to 4 molecules or ethylene oxide. Further anionic surfactants include phosphate derivatives of the ethylene oxide based nonionic surfactants described herein.

It is of considerable advantage that at least a proportion of the anionic surfactant be in liquid form or readily liquifiable.

In many suitable classes of anionic surfactants the counter ion is a monovalent metal ion, often a sodium or potassium ion or a quaternary ammonium cation derived for example from ethanolamine or isopropylamine.

In practice, cationic detergents are normally not present in the same composition as anionic surfactants, but when cationic detergents are used they are frequently quaternary ammonium salts such as tetraalkyl ammonium salts in which at least one of the alkyl group contains at least 10 carbon atoms or quaternary pyridinium salts substituted by an alkyl chain of at least 10 carbon atoms. Although quaternary ammonium halides, commonly chlorides, can be employed, particularly where the quaternary ammonium halide and ester peracid are combined shortly before use, in many embodiments it is preferred to employ non-halide quaternary ammonium salts. The use of non-halide quaternary ammonium salts is particularly preferred where the solution containing the ester peracid and quaternary ammonium salt are to be stored for any significant period. The use of quaternary ammonium halides in such solutions for storage can cause decomposition of the ester peracid by oxidation of the halide. Examples of non-halide quaternary ammonium salts include sulphates, methosulphates, ethosulphates, hydroxides, acetates, saccharinates, phosphates and propionates.

A considerable proportion of nonionic surfactants suitable for use in the present invention comprises condensation products of ethylene oxide and possibly propylene oxide. One class of such nonionic surfactants which is of special importance comprises water soluble condensation products of alcohols containing from 8 to 18 carbon atoms with an ethylene oxide polymer often containing at least 5 moles of ethylene oxide per molecule of surfactants, e.g. from 7 to 20 moles of ethylene oxide. Other nonionic surfactants comprise water soluble condensates of alkyl phenols or alkyl naphthols with an ethylene oxide polymer normally containing from 5 to 25 moles of ethylene oxide per mole of alkyl phenol or alkyl naphthol. The alkyl group normally contains from 6 to 12 carbon atoms and is frequently linear. As an alternative to the hydrophobic moiety of the nonionic surfactant being linked to the hydrophilic moiety by an ether link as in alcohol or phenol/ethylene oxide condensates, the linkage can be an ester group. The hydrophobic moiety is normally the residue of a straight chain aliphatic acid containing from 8 to 22 carbon atoms and more particularly lauric, stearic and oleic residues. In one class of nonionic ester surfactants, the hydrophilic moiety often comprises polyethylene oxide, frequently in the ratio of from 5 to 30 moles of ethylene oxide per mole of the fatty acid residue. It will be recognised that both mono and di esters can be employed. Alternatively it is possible to employ as the hydrophilic moiety glycerol, thereby producing either mono or di glycerides. In a further group, the hydrophilic moiety comprises sorbitol. A further class of nonionic surfactants comprise alkanolamides which can be obtained when a C10 to C22 amide is condensed with a polyethylene oxide or polypropylene glycol hydrophilic moiety or moieties Semipolar detergents include water soluble amine oxides, water soluble phosphine oxides and water soluble sulphur oxides, each containing one alkyl moiety of from 10 to 22 carbon atoms and two short chain moieties selected from the groups of alkyl and hydroxyalkyl groups containing 1 to 3 carbon atoms.

Useful amphoteric surfactants include derivatives of aliphatic quaternary ammonium, sulphonium and phosphonium compounds in which the aliphatic moieties can be linear or branched or two of which can join to form a cyclic compound, provided that at least one of the constituents comprises or contains a hydrophobic group containing from about 8 to 22 carbon atoms and the compound also contains an anionic water solubilising group, often selected from carboxylic, sulphate and sulphonates.

Non-surfactant thickeners which may be employed comprise cross linked poly(acrylates), natural gums such as xanthan or rhamsan gum, cellulose derivatives such as carboxymethyl cellulose and silicates.

The method for disinfection according to the present invention comprises contacting the substrate to be disinfected with a solution of a storage stable, aqueous acidic solution of an ester peracid, or prepared from one. The solution may be employed without dilution, or may be diluted. When the compositions are diluted, the dilution is usually chosen to give a concentration of ester peracid in solution of between about 1 part per million and 10,000 parts per million, depending on the substrate.

The disinfecting method may utilise a very wide range of temperatures, typically ranging from about 4° C. to the boiling point of the solution employed as a disinfectant. In many cases, especially if the disinfectant is being applied manually using, e.g. a cloth, the temperature will be limited by the maximum temperature which can be tolerated comfortably by the operative, and is unlikely to be greater than 60° C.

The disinfection process can be employed to treat a wide range of substrates. Many of the treatable substrates are either liquid or solid. A contaminated gaseous substrate can be treated conveniently by spraying with a dilute solution of the invention biocidal combination or by bubbling the gas through a bath of the invention peracid solution. One type of liquid substrate comprises micro-organism contaminated aqueous media such as recirculating process waters, or aqueous effluents prior to discharge. Such process waters and effluents occur in many different industries and can be contaminated by bacteria, algae, yeasts and more rarely by viruses Without limiting to the following industries, contaminated process waters are prevalent during the processing of plant and animal materials, including the paper and pulp industries, food processing eg the sugar refining industry, brewing, wine-making and alcohol distilling industries, effluents from straw treatments, discharges from sewage treatment works, including partially treated or merely filtered discharges of sewage through pipelines extending out to sea, meat processing factories, carcass rendering activities and from the rearing of livestock. Other liquid substrates include irrigation water in the horticulture industry. A further important source of contaminated aqueous media comprises cooling waters either industrially or arising from air conditioning units installed in large buildings, such as hotels, offices and hospitals. The invention compositions can be employed to treat non-aqueous liquid media, such as cutting oils.

Notwithstanding the foregoing, the invention compositions are seen as of particular value for disinfection in those areas which come into contact with humankind. Thus they can be employed to disinfect solids, including hard surfaces, or contaminated articles intended for re-use in the food processing, animal rearing, horticulture, catering, domestic or hospital environments. Hard surfaces can be made from metals, wood, ceramics, glass, and plastics and can include work-benches, walls, floors, sanitary ware (eg toilets and basins), plant or apparatus, containers, tools, machinery, plant and pipework. It will be recognised that for such hard surfaces, it is often convenient to immerse smaller articles in a solution of the invention biocidal composition, and for larger applications, a spray or the like distribution means can be easier to employ The process can also be contemplated for disinfecting water absorbent materials such as infected linen or especially soiled babies' nappies that are often made from terry toweling. The invention compositions can be used to disinfect harvested plants or plant products including seeds, corms, tubers, fruit, and vegetables. Alternatively, the invention compositions can be used to treat growing plants, and especially crop growing plants, including cereals, leaf vegetables and salad crops, root vegetables, legumes, berried fruits, citrus fruits and hard fruits.

It will none the less also be recognised that the peracid solutions produced by the invention process may also be employed, if desired, for the other purposes for which peracids are used, including bleaching or as a bleach additive in washing processes.

Having described the invention in general terms, specific embodiments thereof are described in greater detail by way of example only.

EXAMPLES 1 TO 6, AND COMPARISONS CA1-6 AND CB1-6

In Example 1, a mixture of the dimethyl esters of respectively succinic, glutaric and adipic acids (16%, 58% and 26%, 106 g). available under the name DBE from Dupont was stirred at ambient temperature (about 22° C.) with demineralised water [DMVW] (594.2 g) and sulphuric acid (10 g, 98% w/w) and aqueous hydrogen peroxide (285.6 g, 35% w/w) was introduced slowly into the stirred mixture at such a rate that the solution temperature was kept at or close to 20° C. The resultant solution contained a significant concentration of the corresponding monoperacid derivatives of succinic glutaric and adipic as the predominant peracid species and residual hydrogen peroxide. In Examples 2 to 6, the stabilisers shown in Table 1 below were mixed into portions of the solution obtained in Example 1.

The stability of the solutions was tested by transferring 120 g of the solution into a screw capped HDPE bottle having a small vent hole and storing them in a dark temperature controlled enclosure. The available oxygen in the solution (avox) was measured initially and at 4 weekly intervals by a standard ceric sulphate titration method.

By way of comparison, the preparative process of Example 1 was followed but substituting for the DBE a mixture of monomethyl glutarate (53 g), monomethyl adipate (26.5 g) and monomethyl succinate (26.5 g) from Aldrich Chemicals in CA and a mixture of succinic glutaric and adipic acids (106 g) obtained from BASF in CB. Similarly, solutions containing the same stabilisers were prepared from the unstabilised comparison solutions. The residual avox of the Comparison solutions is likewise shown in Table 1.

TABLE 1

| | Stabiliser | | Storage | % Avox Retained | | |
|---|---|---|---|---|---|---|
| No | Type | weight g | weeks | Example | CA | CB |
| 1 | — | — | 4 | 91.2 | 88.3 | 51.3 |
| | — | — | 8 | 89.9 | 76.7 | 28.3 |
| 2 | pHBA | 0.12 | 4 | 98.6 | 96.7 | 74.0 |
| | " | 0.12 | 8 | 97.5 | 95.9 | 50.2 |
| 3 | HEDPA | 0.20 | 4 | 96.7 | 90.9 | 57.7 |
| | " | 0.20 | 8 | 92.2 | 78.6 | 30.7 |
| 4 | pHBA + HEDPA | 0.12 + 0.20 | 4 | 99.6 | 98.5 | 77.3 |
| | pHBA + HEDPA | 0.12 + 0.20 | 8 | 100 | 96.3 | 54.6 |
| 5 | ADPA | 0.20 | 4 | 94.9 | 90.2 | 53.5 |
| | " | 0.20 | 8 | 89.3 | 78.7 | 30.6 |
| 6 | ADPA + pHBA | 0.20 + 0.12 | 4 | 100 | 97.4 | 77.6 |
| | ADPA + pHBA | 0.20 + 0.12 | 8 | 99.3 | 96.8 | 55.5 |

Herein, pHBA represents p-hydroxybenzoic acid HEDPA and ADPA each represents a commercially available grade of hydroxyethylidene-diphosphonic acid.

From Table 1, it can be seen that preparative method according to the present invention produced a more stable peracid solution with respect to the retention of avox than when the peracid solution was made from either the corresponding monoester of the dicarboxylic acid (CA) or the dicarboxylic acid itself (CB). It can also be seen that the same advantage was evident when the solution additionally contained stabilisers intended for peracids

EXAMPLES 7 TO 11

In these Examples, all of the constituents shown in Table 2 except the hydrogen peroxide were mixed together at ambient temperature in a high density polyethylene (HDPE) bottle and immediately after, the hydrogen peroxide was introduced very gradually to prevent the temperature rising more than a few degrees over 20° C. The surfactant was that available under the trade mark CAFLON NAS30. The bottle's cap was then fitted, and the solutions were analyzed for total avox (the avox from peracids and hydrogen peroxide), avox from solely peracids and by HPLC to distinguish between monoester peracid and acidperacids species present The bottles were stored in the dark in a constant temperature enclosure set at 32° C. The residual total avox after 4 weeks' storage and the weight ratio (WR) of ester peracid acid peracid are shown in Table 2.

TABLE 2

| | Amount (g) present in | | | | |
|---|---|---|---|---|---|
| Constituent | Ex 7 | Ex 8 | Ex 9 | Ex 10 | Ex 11 |
| DBE-5 | 120 | 75 | 75 | 22.5 | 22.5 |
| $H_2O_2$ 35% | 21.43 | 64.3 | 21.43 | 64.3 | 21.43 |
| DMW | 8.57 | 10.7 | 53.57 | 63.2 | 106.07 |
| $H_2SO_4$ (98%) | 1.5 | 1.5 | 1.5 | 1.5 | 1.5 |
| pHBA | 0.018 | 0.018 | 0.018 | 0.018 | 0.018 |
| butyl triglycol | 1.5 | 1.5 | 1.5 | 1.5 | 1.5 |
| surfactant | 3 | 3 | 4.5 | 1.5 | 1.5 |
| % Avox Recovered | 85.0 | 85.6 | 94.7 | 93.8 | 94.2 |
| % peracid | 4.5 | 9 | 3 | 2.6 | 1 |
| WR ester per acid: acid peracid | 3.0 | 1.6 | 0.7 | 0.2 | 0.2 |

From Table 2, it can be seen that peracid solutions can be obtained with an excellent retention of active oxygen species (as shown by the near 100% avox retention) over a wide range of ratios of diester substrate to hydrogen peroxide. From Table 2, it can also be seen that as the weight ratio of hydrogen peroxide to diester acid substrate increases and the dilution of the solution increases, there is a distinct tendency for acid peracid to be favoured relative to monoester peracid, whereas as the weight ratio of diester acid substrate to hydrogen peroxide increases and the concentration of substrate in the solution increases there is a distinct tendency for the monoester peracid to be favoured relative to the acid peracid.

In repeat trials at a higher addition of stabiliser, an enhanced avox stability was observed.

EXAMPLES 12 TO 14

In Example 12, a relatively concentrated solution of peracids was obtained by introducing with agitation, concentrated hydrogen peroxide (4.7 g, 85% w/w) into DBE (20 g) and sulphuric acid (98% w/w, 0.2 g) at ambient temperature, the rate of introduction being controlled to prevent the mixture temperature rising. The solution was stored in a screw capped HDPE bottle and the peracid and total avox concentrations were periodically measured by the standard methods used for Examples 7 to 11. The results for 1 day and 6 weeks are summarised below.

The process of Example 12 was repeated for Examples 13 and 14, but employing respectively 5.7 g 70% w/w hydrogen peroxide and 0.3 g sulphuric acid in Ex 13 and 7.99 g hydrogen peroxide (50% w/w) and 0.4 g sulphuric acid in Ex 14.

The results are summarised in Table 3 below.

| | Avox measured after | | | | | |
|---|---|---|---|---|---|---|
| Example | 1 day | | 3 weeks | | 6 weeks | |
| No | peracid | total | peracid | total | peracid | total |
| 12 | 2.6 | 10.2 | 2.4 | 8.0 | 2.6 | 6.1 |
| 13 | 2.4 | 10.9 | 2.4 | 10.2 | 2.9 | 6.2 |
| 14 | 2.0 | 11.5 | 1.8 | 10.0 | 2.0 | 9.5 |

From Table 3, it can be seen that solutions generated in each Example contained within 1 day a high concentration of peracid species. The Table also shows that the compositions maintained their peracid concentration at a steady level for the 6 weeks storage. HPLC analysis of the solutions showed that after 3 weeks, approximately ⅓rd of the diester had been converted to the ester peracid in each of Examples 12 to 14, 36%, 38% and 35% respectively and that after 6 weeks storage, the proportion of esterperacid had fallen by about 2%. The HPLC analyses also showed that at the concentrations of catalyst used, the solutions were substantially free from monomethylpersuccinic acid.

EXAMPLES 15 TO 20

In these Examples, Example 12 was repeated but employing 0.4 g of stated acid catalyst in the mixture and storage at either ambient or 40° C. The compositions were stored in dark at the formation temperature. The results are summarised in Table 4 below.

TABLE 4

| Example no | Acid Catalyst | Temperature | Peracid Avox after 1 day | 2 weeks |
|---|---|---|---|---|
| 15 | H$_2$SO$_4$ | ambient | 3.0 | 3.1 |
| 16 | H$_2$SO$_4$ | 40 | 2.8 | 2.8 |
| 17 | MSA | ambient | 2.8 | 3.0 |
| 18 | MSA | 40 | 2.7 | 2.8 |
| 19 | p-TSA | ambient | 2.6 | 2.7 |
| 20 | p-TSA | 40 | 2.7 | 2.6 |

From Table 4, it can be seen that a very similar concentration of peracid is obtained using the range of catalysts and temperature conditions shown, and that the concentration is maintained, even at mildly elevated temperature over the period of time of the trial.

EXAMPLES 21 AND 22

In Example 21, The process of Example 1 was repeated, but employing 100 g of the mixed ester DBE.

In Example 22, a dilute peracid composition was produced in two stages. In the first stage, concentrated hydrogen peroxide solution (HTP grade, 85% w/w, 25 g) was introduced slowly with stirring into DBE-5 (100 g) containing conc. sulphuric acid (1 g) and with cooling to prevent the mixture rising significantly above room ambient temperature, and this was stored overnight at ambient temperature, about 20–23C, by which time greater than 90% of the equilibrium amount of peracid had been produced. A fraction of the mixture (10 g) was then diluted at ambient by introduction with stirring of demineralised water (71.4 g) and a further amount of HTP (8 g), to provide a product which comprised in terms of the reactants 10% w/w diester and 10.5% hydrogen peroxide. The product was stored at ambient temperature in a screw capped HDPE bottle and analyzed for peracids periodically. The results are summarised in Table 5 below.

TABLE 5

| | % w/w total peracids | % w/w ester peracid |
|---|---|---|
| Ex 21 | 1.0 | 0.2 |
| Ex 22 after 1 week | 3.0 | 2.7 |
| Ex 22 after 3 weeks | 1.0 | 1.0 |

It can be observed from Table 5 that the method employed in Example 22 resulted in the preparation of a composition containing a higher concentration of ester peracid, and that this advantage was maintained even after 3 weeks' storage by which time the total peracid content had fallen to that obtained by a one stage preparation route of Example 21.

EXAMPLES 23 TO 28

In these Examples, compositions were made by stirring together in a flask at ambient temperature diester (DBE-5) or mixture of diesters (DBE) with laboratory grade sulphuric acid (98% w/w) demineralised water (DMW) and aqueous hydrogen peroxide (HTP-85% w/w H$_2$O$_2$) until a single phase was observed, the stabilisers were introduced and the mixture stirred for a further 10 minutes. The constituents are summarised in Table 6 below.

| Constituent | Example No 23 | 24 | 25 weight (g) | 26 | 27 | 28 |
|---|---|---|---|---|---|---|
| DBE-5 | 14 | | 30 | | 160 | |
| DBE | | 14 | | 30 | | 160 |
| DMW | 167.5 | 167.5 | 92 | 92 | 2.7 | 2.7 |
| sulphuric acid | 2 | 2 | 1.5 | 1.5 | 2 | 2 |
| HTP | 16.5 | 16.5 | 26.5 | 26.5 | 35.3 | 35.3 |
| pHBA | 0.2 | 0.2 | 0.15 | 0.15 | 0.2 | 0.2 |
| ADPA | 0.8 | 0.8 | 0.6 | 0.6 | 0.8 | 0.8 |

The compositions were then stored at ambient temperature in HDPE bottles.

EXAMPLES 29 TO 34 AND COMPARISONS 35 TO 37

In these Examples and comparisons, the disinfectant capabilities of the compositions of Examples 23 to 28 were measured and compared with the performance of disinfectant compositions obtained in a similar manner, but substituting glutaric acid for DBE-5 in respectively Example 23/25 (Comparison 35/36) and a mixture of succinic, glutaric and adipic acids for DBE in Example 24 for Comparison 37. The compositions were at least 1 month old when they were tested.

Test Method

These tests were conducted according to the American Organisation of Analytical Chemists official method of analysis 960.09 of 1990, modified by I) employing sodium thiosulphate (50 g/l) as neutraliser, together with catalase at 2–5 g/l a solution dilution of 9:1 and ii) culturing in a sterile Universal culture jar.

The results obtained with total peracid content of 100 ppm are summarised in Table 7 below.

| Example No | Composition obtained in | LRF against S. aureus | LRF against E. coli |
|---|---|---|---|
| 29 | 23 | 1.85 | 2.39 |
| 30 | 24 | 3.61 | 2.15 |
| 31 | 25 | 2.05 | 3.49 |
| 32 | 26 | 3.81 | 3.31 |
| 33 | 27 | 2.32 | 2.89 |
| 34 | 28 | 4.16 | 4.23 |
| Comp 35 | | 1.16 | 3.53 |
| Comp 36 | | 0.93 | 3.25 |
| Comp 37 | | 1.03 | 3.46 |

From Table 6, it can be seen that the compositions according to the invention were effective disinfectants and that the benefit was especially observable in compositions which contained a significant fraction of ester peracid compared with compositions which contained a higher proportion of acid peracid. The compositions were also particularly effective against S. aureus and were generally of similar effectiveness against E. coli compared with the compositions generated from the dicarboxylic acid as starting material.

EXAMPLES 38 AND 39

In these Examples, further compositions according to Example 23 were made by the same route, but substituting respectively 15 g water by sulphamic acid and 18 g water by phosphoric acid. The resultant compositions were able to function as both a disinfectant and lime-scale remover.

EXAMPLES 40 AND 41

In these Examples, a two stage route was employed to make disinfectant compositions. In the first stage, aqueous hydrogen peroxide (44.4 g, 33.8%) was agitated with respectively DBE-5 or DBE (20 g) at 35° C. and a stabiliser system comprising 0.1% p-HBA and 0.2% ADPA until a clear single phase was observable and in the second stage at the same temperature was diluted with DMW (35 g) at such a rate as to maintain a single phase system. It was observed that the first stage took about 1 hour in Example 40 and 75 minutes in Example 41, and the second stage took about 1 hour in each case.

This route represented a comparatively quick way to produce single phase compositions.

EXAMPLE 42

In this Example, the anti-microbial activity against mould spores *Aspergillus niger* of an invention composition was measured under a modified version of CEN method EN1040. The method was modified by testing 4 different concentrations of the peracid constituent instead of 3. The weighted mean counts were not calculated and the full Test report was not completed. The method was extended to include the evaluations of yeasts, because the specific method for yeasts had not been published by then.

The peracid composition which was tested was made using the method described in Example 1 using DBE-5 (424 g). demineralised water (2377 g), sulphuric acid (40 g, 98%), $H_2O_2$ (1142 g, 35%) and p-HBA (4 g). This was stirred for 4 hours at ambient to ensure complete homogeneity. The product contained 9% $H_2O_2$ and 1.4% peracid at equilibrium.

The modified CEN method EN1040 was conducted under both clean and dirty conditions The tests showed that the composition reduced the viable population of *Asperigillus niger* (spores) in the test by an LRF of above 4 under both clean and dirty conditions, not only when applied neat, but also when diluted by a factor of 4.

EXAMPLE 43

In this example, the general method of Example 1 was followed using diethyl glutarate (7 g), $H_2O_2$ (8.24 g, 85%), sulphuric acid (1 g, 98%) and demineralised water (83.8 g). After stirring for 1 week at ambient. p-HBA (0.1 g) and ADPA (0.17 g) were added. The sample contained 7.82% $H_2O_2$ and 0.88% peracid.

EXAMPLE 44

In this Example, the general method of Example 1 was followed at 30° C. using dimethyl fumarate (7 g), $H_2O_2$ (85%, 8.24 g), sulphuric acid (1 g, 98%), demineralised water (83.8 g) forming a suspension of diester in the aqueous medium. p-HBA (0.1 g) and ADPA (0.17 g) were added and after stirring for 7 hours at 30° C., the aqueous medium contained 0.3% peracid.

What is claimed is:

1. A process for the production of aqueous percarboxylic acid solutions by reaction of a peroxygen compound and a precursor of the percarboxylic acid in the presence of an acid catalyst wherein the peroxygen compound comprises hydrogen peroxide and the precursor comprises an aliphatic diester satisfying the general formula $R^1$—O—CO—$R^2$—CO—O—$R^3$ wherein $R^1$ and $R^3$ each represents an alkyl group containing from 1 to 4 carbon atoms which may be the same or different and $R^2$ represents an alkylene group which may be linear or branched containing from 2 to 6 carbon atoms and optionally unsaturated, and wherein the reaction mixture expressed in terms of its reactants comprises at least 3% diester.

2. The process according to claim 1 wherein the reaction mixture expressed in terms of its reactants comprises from 5 to 90% w/w diester.

3. The process according to claim 1 wherein the reaction mixture expressed in terms of its reactants comprises hydrogen peroxide selected in the range of up to 30% w/w.

4. The process according to claim 1 wherein the reaction mixture expressed in terms of its reactants comprises at least 4% w/w hydrogen peroxide.

5. The process according to claim 1 wherein the reaction mixture expressed in terms of its reactants comprises at least 1 mole of hydrogen peroxide per 4 moles of diester.

6. The process according to claim 5 wherein the mole ratio of hydrogen peroxide:diester is selected in the range of from 10:1 to 1:4.

7. The process according to claim 6 wherein at least an equimolar amount of hydrogen peroxide is employed per mole of diester.

8. The process according to claim 1 wherein the reaction mixture expressed in terms of its reagents comprises at least 50% w/w diester.

9. The process according to claim 8 wherein the reaction mixture expressed in terms of its reagents comprises from 70 to 85% w/w diester and from 1 to 1.25 moles of hydrogen peroxide per mole of diester.

10. The process according to claim 1 wherein the reaction mixture expressed in terms of its reagents and water comprises from 50 to 90% w/w water, hydrogen peroxide selected in the range of from 4 to 25% w/w and diester selected in the range of from 5 to 45% w/w.

11. The process according to claim 10 wherein the weight ratio of diester to hydrogen peroxide is selected in the range of 4:1 to 2:3.

12. The process according to claim 10 wherein the reaction mixture expressed in terms of its reagents and water comprises 75 to 85% water and hydrogen peroxide selected in the range of from 4 to 12% w/w and diester selected in the range of from 5 to 15% w/w.

13. The process according to claim 1 conducted in at least two stages, in the first stage of which a reaction mixture is employed which expressed in terms of its reactants comprises at least 50% w/w diester and at least 1 mole of hydrogen peroxide per mole of diester, said mixture being stored until at least 75 molar % of the equilibrium proportion of peracid species is attained and thereafter the mixture is diluted with water and optionally at least one of the reactants to produce a composition comprising at least 50% w/w water.

14. The process according to claim 13 wherein the diluted mixture contains, expressed in terms of the reactants, a total of 5 to 15% w/w diester and 4 to 12% w/w hydrogen peroxide.

15. The process according to claim 1 wherein the solution is stored before use until its percarboxylic acid content reaches or exceeds at least 90% of the amount of percarboxylic acid present at equilibrium.

16. The process according to claim 1 wherein aqueous hydrogen peroxide is introduced into diester at a rate controlled to maintain the mixture as a single phase.

17. The process according to claim 16 wherein the aqueous hydrogen peroxide has a concentration selected in the range of from 27 to 55% w/w $H_2O_2$.

18. The process recording to claim 16 wherein water is introduced into the mixture of diester and hydrogen peroxide at a rate controlled to maintain the mixture as a single phase.

19. The process according to claim 16 wherein the proportion of water provided in total from the aqueous hydrogen peroxide and the water is at least 50% by weight of the final composition.

20. The process according to claim 1 wherein the solution has a pH of from −2 to 1.

21. The process according to claim 1 wherein, in the formula, $R^1$ and $R^3$ are each selected from methyl and ethyl groups.

22. The process according to claim 21 wherein $R^1$ and $R^3$ are both methyl.

23. The process according to claim 1 wherein, in the formula, $R^2$ is saturated.

24. The process according to claim 1 wherein, in the formula, $R^2$ is selected from linear groups containing from 2 to 4 carbon atoms and mixtures of any two or all three of them.

25. The process according to claim 1 wherein the reaction mixture contains up to 10% w/w of an acid introduced before, during or after the reaction.

26. The process according to claim 1 wherein the reaction mixture contains from 0.1 to 2.5% w/w of an inorganic or organic acid catalyst having a $pK_a$ of below 1.

27. The process according to claim 1 wherein the reaction mixture contains from 0.025 to 1% w/w of at least one stabiliser selected from hydroxy-substituted aromatic carboxylic acids and their ester derivatives, and organic polyphosphonic acids or mixtures of any two or more thereof.

28. The process according to claim 27 wherein the hydroxy-substituted aromatic carboxylic acid comprises p-hydroxy benzoic acid, and the organic polyphosphonic acid comprises hydroxyethylidenediphosphonic acid or ethylene or cyclohexane diaminotetramethylene phosphonic acid or diethylene triaminopentamethylene phosphonic acid.

29. The process according to claim 1 wherein the reaction mixture contains at least one surfactant introduced before, during or after the reaction.

30. A composition comprising an ester, a peracid derivative thereof, hydrogen peroxide and water comprising at from 2 to 30% w/w hydrogen peroxide, 5 to 90% w/w water and 3 to 90% w/w of an aliphatic diester satisfying the general formula $R^1$—O—CO—$R^2$—CO—O—$R^3$ in which $R^1$ and $R^3$ each represents an alkyl group containing from 1 to 4 carbon atoms which may be the same or different and $R^2$ represents an alkylene group which may be linear or branched containing from 2 to 6 carbon atoms and optionally unsaturated, the % w/w for the diester including the peracidic derivative thereof and any acidic derivative of the ester generated in situ, the composition including a residual concentration of the diester.

31. The composition according to claim 30 comprising at least 0.1% w/w ester peracid.

32. A composition containing hydrogen peroxide, a peracid and an ester and hydrolysis perhydrolysis derivatives thereof comprising at least 2% w/w hydrogen peroxide, and at least 3% w/w diester including hydrolysis and perhydrolysis derivatives thereof, of which at least 0.1 is an ester peracid, the composition including a residual concentration of the diester.

33. The composition according to claim 30 wherein the concentration of hydrogen peroxide is not more than 20% w/w.

34. The composition according to claim 33 wherein the concentration of hydrogen peroxide is from 4to 12%.

35. The composition according to claim 30 wherein the concentration of diester and its derivatives is from 3 to 15% w/w.

36. The composition according to claim 30 wherein the weight ratio of diester and derivatives thereof to hydrogen peroxide is selected in the range of from 4:1 to 2:3.

37. The composition according to claim 36 wherein the diester is a dimethyl.

38. The composition according to claim 30 wherein $R^2$ in the formula for the diester represents an alkylene group containing from 2 to 4 carbons or a mixture of any 2 or 3 such diesters.

39. The composition according to claim 30 comprising additionally a surfactant.

40. The composition according to claim 30 containing from 0.025 to 1% w/w of at least one stabiliser selected from hydroxy-substituted aromatic carboxylic acids and their ester derivatives, and organic polyphosphonic acids or mixtures of any two or more thereof.

41. The composition according to claim 30 comprising additionally a non halide mineral acid selected from sulphuric or phosphoric or sulphamic acid or an organic sulphonic acid at a concentration of from 0.05 to 10% w/w.

42. A composition comprising an ester, a peracid derivative thereof, hydrogen peroxide and water comprising from 2 to 30% w/w hydrogen peroxide, 5 to 90% w/w water and 3 to 90% w/w of an aliphatic diester satisfying the general formula $R^1$—O—CO—$R^2$—CO—O—$R^3$ in which $R^1$ and $R^3$ each represents an alkyl group containing from 1 to 4 carbon atoms which may be the same or different and $R^2$ represents an alkylene group which may be linear or branched containing from 2 to 6 carbon atoms and optionally unsaturated, the % for the diester including the peracidic derivative thereof and any acidic derivative of the ester generated in situ and containing a C1 to C4 alcohol in the range of from 1 to 20% w/w and at a mole ratio to the aliphatic diester of greater than 1:1.

43. The process according to claim 3 wherein the reaction mixture expressed in terms of its reactants comprises no more than 20% w/w hydrogen peroxide.

44. The process according to claim 9 wherein the reaction mixture expressed in terms of its reactants comprises from 75 to 85% w/w diester.

45. The process according to claim 13 wherein the reaction mixture comprises at least an equimolar amount of hydrogen peroxide and diester.

46. The process according to claim 13 wherein the resultant composition comprises at least 75% w/w water.

47. The composition according to claim 31 comprising from 0.3 to 3% w/w ester peracid.

48. The composition according to claim 36 wherein the weight ratio of diester and derivatives thereof to hydrogen peroxide is from 3:2 to 2:3.

49. The composition according to claim 39 wherein said surfactant comprises up to 20% w/w.

50. The process according to claim 1 conducted in at least two stages, in the first stage of which aqueous hydrogen peroxide and the diester are agitated together to form a single phase, and in the second stage of which the phase is diluted with water and again agitated until a single phase is obtained.

51. The composition wording to claim 30 wherein the diester comprises a mixture of diesters of succinic acid, glutaric acid and adipic acid.

52. The composition according to claim 51 wherein the mixture of diesters comprises 10–20% w/w of succinic acid, 40–70% w/w of glutaric acid and 20–33% w/w of adipic acid.

* * * * *